United States Patent [19]

Swerdloff et al.

[11] Patent Number: 4,629,491

[45] Date of Patent: Dec. 16, 1986

[54] OXIDIZED SULFUR DERIVATIVES OF DIAMINOPHOSPHINYL COMPOUNDS AS UREASE INHIBITORS AND UREASE INHIBITED UREA BASED FERTILIZER COMPOSITIONS

[75] Inventors: Michael D. Swerdloff, Parsippany; Milorad M. Rogic, Whippany, both of N.J.; Larry L. Hendrickson, Camillus, N.Y.

[73] Assignee: Allied Corporation, Morris Township, Morris County, N.J.

[21] Appl. No.: 563,347

[22] Filed: Dec. 20, 1983

[51] Int. Cl.$^4$ ............... A01N 57/26; A61K 31/66; C07F 9/02
[52] U.S. Cl. ........................... 71/87; 514/89; 514/90; 514/107; 514/108; 514/112; 514/113; 514/116; 514/117; 514/118; 514/120; 514/125; 514/127; 514/128; 544/157; 546/22; 558/386; 560/13; 560/150; 564/14
[58] Field of Search ............. 564/14; 424/220, 216; 260/465 E; 71/87; 514/89, 90, 107, 108, 112, 113, 116, 117, 118, 120, 125, 127, 128; 544/157; 546/22; 558/386; 560/13, 150

[56] References Cited

U.S. PATENT DOCUMENTS

| | | | |
|---|---|---|---|
| 4,182,881 | 1/1980 | Bayless et al. | 546/22 |
| 4,222,948 | 9/1980 | Alaimo et al. | 260/397.7 R |
| 4,225,526 | 9/1980 | Alamoi et al. | 260/397.7 R |
| 4,242,325 | 12/1980 | Bayless et al. | 424/210 |

FOREIGN PATENT DOCUMENTS

| | | |
|---|---|---|
| 122177 | 9/1976 | German Democratic Rep. |
| 122621 | 10/1976 | German Democratic Rep. |
| 130936 | 5/1978 | German Democratic Rep. |
| 142714 | 7/1980 | German Democratic Rep. |
| 1494774 | 12/1977 | United Kingdom |

OTHER PUBLICATIONS

M. Nakanishi and T. Oe, Japan Patent 7379, Chem. Abstr. 1967, vol. 67, 81947x.

*Primary Examiner*—Dolph H. Torrence
*Attorney, Agent, or Firm*—Richard C. Stewart; Gerhard H. Fuchs

[57] ABSTRACT

The invention relates to novel urease inhibited fertilizer compositions containing urea and a urease inhibiting amount of one or more diaminophosphinyl compounds having oxidized sulfur functions, and methods and composition for inhibiting the activity of urease through use of such compounds.

26 Claims, No Drawings

OXIDIZED SULFUR DERIVATIVES OF DIAMINOPHOSPHINYL COMPOUNDS AS UREASE INHIBITORS AND UREASE INHIBITED UREA BASED FERTILIZER COMPOSITIONS

BACKGROUND OF THE INVENTION

1. Field of the Invention

This invention relates to urease inhibited urea based fertilizer compositions. More particularly, this invention relates to urease inhibited urea based fertilizer compositions which contain certain diaminophosphinyl compounds containing oxidized sulfur functions, as the urease inhibitors, and to methods and compositions for inhibiting the action of soil urease through use of such compounds.

2. The Prior Art

It is well known in the art to use urea and urea compositions in fertilizers, for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonia, when urea is placed under or on the surface of soil which contains urease. Urease, a crystallizable enzyme occurring in numerous bacteria and fungi, as for example *Micrococcus urease,* catalyzes the conversion of urea into ammonia and carbon dioxide. The reactions are as follows:

A portion of the ammonia thus formed is held by absorbing constituents of the soil and is available to plants as nutrient. However, a large amount of the ammonia may be lost to the air. A further problem resulting from the action of urease is the accumulation of ammonium in the soil which can damage germinating seedlings and young plants.

One approach to the reduction of problems resulting from the activity of soil urease toward soid applied urea is to find compounds that inhibit urease activity when applied to soils in conjunction with fertilizer urea. This approach has received considerable attention, and several classes of compounds have been used as urease inhibitors.

For example, certain prior art describes various phosphoro compounds which are useful as urease inhibitors. Illustrative of such prior art are East German Pat. Nos. 142,714; 212,026; 122,177; 122,621 and 130,936, and Great Britain Pat. No. 1,494,774 which describe various phosphorodiamidate compounds as urease inhibitors. Also exemplary of such prior art is U.S. Pat. No. 4,242,325 which describes a method of controlling the enzymatic decomposition of urea to ammonia and carbonic acid due to the action of urease which comprises exposing the enzyme to certain phosphoric triamide compounds. U.S. Pat. No. 4,182,881 describes the use of certain N-[diaminophosphinyl]arylcarboxyamide compounds as inhibitors of the enzyme urease in the urinary tract. U.S. Pat. No. 4,225,526 describes the use of 8-[(4-aminophenyl)sulfonyl]amino-2-naphthalenyl phosphorodiamidate compounds as inhibitors of the enzyme urease, and U.S. Pat. No. 4,222,948 describes the use of ([(4-aminophenyl)sulfonyl]amino)phenyl phosphorodiamidates as inhibitors of the enzyme urease. Nakanishi, M, and Oe, T, Japan Pat. No. 7379; Chem. Asbtr. 1967, 67, 81947X describes certain diaminophosphinyl compounds containing oxidized sulfur functions and discloses that such compounds are useful in treating diabetes mellitus.

SUMMARY OF THE INVENTION

In accordance with the present invention, there is provided a unique fertilizer composition comprising urea or one or more compounds which are capable of forming urea in situ when subjected to the use conditions of the composition, and a "urease inhibiting effective amount" of one or more compounds of the formula:

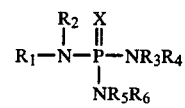

wherein:
X is oxygen or sulfur;
$R_1$ is

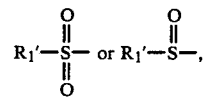

wherein:
$R_1'$ is amino or substituted or unsubstituted alkyl, aryl wherein permissible substituents are selected from the group consisting of one or more alkyl, aryl, halogen, trihalomethyl, nitro, cyano, alkanoyl, alkylcarboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl groups;
$R_2$ is hydrogen, or substituted or unsubstituted alkyl or aryl wherein permissible substituents are as in $R_1'$ above; and
$R_3$, $R_4$, $R_5$ and $R_6$ are the same or different and are hydrogen or alkyl having from about 1 to about 4 carbon atoms.

Hereinafter, the aforementioned compounds are referred to as "oxidized diaminophosphinyl sulfur derivatives".

Another aspect of this invention relates to a method of enhancing the yield of plants which comprises applying the composition of this invention to a plant growth medium within reach of the plant's root system, (hereinafter referred to as "root zone"). The term "plant growth medium" as herein employed refers to various natural and artificial medium which support plant growth, including soil, potting mixtures of organic and inorganic matter, and artificial medium such as polyurethane foams.

Yet another aspect of this invention relates to a composition comprising a "urease inhibiting effective amount" of one or more oxidized diaminophosphinyl sulfur derivatives, which composition is useful for carrying out the aformentioned method. As used herein "urease inhibiting effective amount" is an amount of one or more of the said oxidized diaminophosphinyl sulfur derivatives compounds which when admixed with urea (or one or more urea precursor compounds capable of forming urea in situ under the use conditions of the composition); or when applied to a situs, as for example a plant growth medium, is capable of inhibiting the catalytic activity of urease that may be in or at the medium or other situs to any extent.

It has been discovered by applying a urease inhibiting effective amount of one or more of the oxidized diaminophosphinyl sulfur derivatives to a plant growth medium or other situs the urease catalyzed hydrolysis of urea which may be present at the situs to ammonia is suppressed, thereby preventing the rapid loss of urea from the situs or medium. Furthermore, by proper distribution and/or application of the one or more oxidized diaminophosphinyl sulfur derivatives; this action of inhibiting the urease catalyzed hydrolysis of urea to ammonia is effective over a prolonged period of time.

DETAILED DESCRIPTION OF THE INVENTION

The application and/or distribution of a urease inhibiting effective amount of one or more of the above-identified oxidized diaminophosphinyl sulfur derivatives to a situs, such as a plant growth medium, or inclusion thereof in a composition and application and/or distribution of the composition to a situs is essential for the practice of this invention. While, the oxidized diaminophosphinyl sulfur derivatives can be used to inhibit the urease catalyzed hydrolysis of urea at any situs, they are especially useful for such inhibition in an agricultural context by application to a plant growth medium. In these preferred embodiments, usually, an acceptable level of urease inhibition can be achieved if at least about 0.01 parts by weight of said one or more oxidized diaminophosphinyl sulfur derivatives per one million parts by weight of soil or other plant growth medium. Hereinafter the abbreviation "p.p.m." is used to refer to parts by weight of one or more oxidized diaminophosphinyl sulfur derivatives per one million parts by weight of plant growth medium. In the preferred embodiments of this invention, the amount of said one or more oxidized diaminophosphinyl sulfur derivatives distributed in the said medium is from about 0.01 p.p.m. to about 5,000 p.p.m., and in the particularly preferred embodiments of the invention is from about 0.2 p.p.m. to about 1,000 p.p.m. Amongst these particularly preferred embodiments of the invention, most preferred are those embodiments of the invention in which the amount of said one or more oxidized diaminophosphinyl sulfur derivatives distributed in said medium is from about 1 p.p.m. to about 500 p.p.m.

Within the aforementioned limitations, the preferred amounts of the one or more oxidized diaminophosphinyl sulfur derivatives impregnated or distributed in the plant growth medium are dependent upon the particular situation. Thus, in determining the amount to be employed, consideration is made not only of the treatment need, i.e., soil pH, temperature, soil type, and the like, but also of the mode of application to the plant growth medium. When the one or more oxidized diaminophosphinyl sulfur derivatives are to be applied in a broadcast application, the amount in p.p.m. may frequently be less than in row or band application where, for a substantial depth and width within the vicinity of application, there can be a very high concentration of the one or more such compounds. When application is made near the root zone of growing plants, or when application is made immediately prior to seeding or transplanting, the amounts supplied are frequently at a lower rate than when application is made at the end of the growing season to prepare the plant growth medium for the following season. By dispersing very large dosages in the plant growth medium, a prolonged inhibition of urease activity can be obtained over a period of many months. The concentration of the one or more oxidized diaminophosphinyl sulfur derivatives is eventually reduced to a minimum by decomposition in the plant growth medium.

In one method for carrying out the present invention, one or more oxidized diaminophosphinyl sulfur derivatives are distributed throughout the plant growth medium in a broadcast application, such as by spraying, dusting, distributing in irrigation water and the like. In such application, the one or more oxidized diaminophosphinyl sulfur derivatives are supplied in amounts sufficient to permeate the growing area of the medium with a urease inhibiting effective amount of such oxidized diaminophosphinyl sulfur derivatives. In field administration, the one or more "oxidized sulfur diaminophosphinyl derivative" compounds can be distributed in the plant growth medium in an amount and through such cross-section of the medium as to provide for the presence therein of a urease inhibiting effective amount of the one or more oxidized diaminophosphinyl sulfur derivatives. It is usually preferred that the one or more oxidized diaminophosphinyl sulfur derivatives be distributed in the plant growth medium to a depth of at least two inches below the surface of the plant growth medium.

In another method for carrying out the present invention, one or more oxidized diaminophosphinyl sulfur derivatives are administered to the plant growth medium in a band or row application. In such application, administration is made with or without carrier in amounts sufficient to supply to the soil or other plant growth medium a urease inhibiting effective amount of the one or more oxidized diaminophosphinyl sulfur derivatives. After administration with or without discing or dragging, subsequent irrigation or rainfall distributes the one or more oxidized diaminophosphinyl sulfur derivatives throughout the plant growth medium.

In one embodiment of the present invention, the one or more oxidized diaminophosphinyl sulfur derivatives are distributed throughout the growth medium prior to seeding or transplanting the desired crop plant.

In another embodiment, the soil or plant growth medium within the root zone of growing plants is treated with the one or more oxidized diaminophosphinyl sulfur derivatives in an amount effective to inhibit the action of urease, but sublethal to plant growth. By following such practice, no adverse effect is exerted by the one or more oxidized diaminophosphinyl sulfur derivatives upon growth of seeds or plants. Oftentimes, it is desirable to treat the soil adjacent to plants, and this procedure may be carried out conveniently in side-dressing operations.

In a further embodiment of the invention, soil or other plant growth medium is treated with one or more oxidized diaminophosphinyl sulfur derivatives following harvest to prevent rapid loss of urea, and to prevent build-up of soil urease. Such practice conserves the soil nitrogen for the following growing season. In such application, the upper limit is primarily an economic consideration.

In an additional embodiment, the soil or plant growth medium can be impregnated with the one or more oxidized diaminophosphinyl sulfur derivatives in conjunction with the application of urea or one or more urea precursor compounds capable of forming urea in situ on application to the plant growth medium. Urea is a well known, commercially available compound and will not be discussed herein in detail. Illustrative of compounds which are believed to form urea on addition to the soil and are water soluble and formaldehyde condensation products, as for example methylolureas, methyleneureas and mixtures thereof. These products and a method for their preparation is described in detail in Justice U.S. Pat. No. 3,462,256. Still other useful sources of urea are water-insoluble urea formaldehyde condensation products such as ureaform. Illustrative of useful water-insoluble urea and formaldehyde condensation products are those whose preparation and use are described in detail in U.S. Pat. Nos. 3,677,736 and 4,033,745.

The present invention can be carried out by distributing one or more oxidized diaminophosphinyl sulfur derivatives in an unmodified form through a plant growth medium. The present method also embraces distributing one or more such compounds as a constituent in liquid or finely divided solid compositions.

The concentration of the one or more oxidized diaminophosphinyl sulfur derivatives in compositions to be employed for the treatment of a plant growth medium is not critical and can vary considerably provided the required dosage of the effective agents is supplied to the growth medium. In general, good results are obtained with liquid and/or solid compositions containing at least about 0.00001 percent by weight of the one or more oxidized diaminophosphinyl sulfur derivatives. Usually, however, the weight percent of the one or more oxidized diaminophosphinyl sulfur derivatives is from about 0.0001 percent to about 98 percent by weight on the same basis. In the preferred embodiments of the invention, the amount of the one or more oxidized diaminophosphinyl sulfur derivatives in the composition is from about 0.002 to about 50 weight percent, and in the particularly preferred embodiments is from about 0.01 to about 20 weight percent on the aforementioned basis. Liquid or dust compositions in which the one or more oxidized diaminophosphinyl sulfur derivatives is present in higher concentration can be utilized as such or can be employed as concentrate compositions to be diluted to prepare actual treating compositions.

In such practice, the one or more oxidized diaminophosphinyl sulfur derivatives can be modified with one or more additiments or soil treating adjuvants including water, petroleum distillates or other liquid carriers, surface-active dispersing agents, inert finely divided solids, and fertilizers, as for example urea, the aforementioned urea precursor compounds, and reduced nitrogen fertilizers such as ammonium nitrate and ammonia. These adjuvants cooperate with the one or more oxidized diaminophosphinyl sulfur derivatives so as to facilitate the practice of the present invention and to obtain an improved result. Preferred adjuvants are surface-active dispersing agents, inert finely divided solids and urea and/or urea precursor compounds. The amount of urea or urea precursor compound which may be included in the composition of this invention is not critical to the unique advantages thereof, and any amount known to those of skill in the art for use in fertilizers can be used. Normally, the amount employed will vary widely depending on a number of factors, including the times and frequency of application. In the preferred embodiments of the invention, the quantity of urea or urea precursor compound may vary from about 0.5 to about 95 weight percent based on the total weight of the composition and in the particularly preferred embodiments may vary from about 1 to about 50 weight percent on the same basis. In the most preferred embodiments of this invention, the quantity of urea or urea precursor compound will vary from about 3 to about 40 weight percent on the aforementioned basis.

The composition of this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrient and macronutrients which may be deficient in the soil. The composition may also include plant growth regulators, as for example auxins, cytokinins and the like, as well as pesticides, such as insecticides, miticides, herbicides, nemitocides and the like. Moreover, the fertilizer composition can include sources of nitrogen other than urea, as for example ammonium nitrate and the like, and other materials which increase nitrogen efficiency, as for example, other urease inhibitors and nitrification inhibitors. Depending upon the concentration of the one or more oxidized diaminophosphinyl sulfur derivatives, augmented compositions can be distributed in the plant growth medium without further modification or can be considered as concentrates and subsequently diluted with additional inert carriers to produce the ultimate treating composition.

Liquid compositions containing the desired amount of the one or more oxidized diaminophosphinyl sulfur derivatives can be prepared by dispersing the latter in one or more liquid carriers such as water or an organic solvent with or without the aid of a suitable surface active dispersing agent or emulsifying agent. Suitable organic solvents include acetone, diisobutylketone, methanol, ethanol, isopropyl alcohol, diethyl ether, toluene, methylene chloride, chlorobenzene and petroleum distillates. The preferred organic solvents are those which are of such volatility that they leave little permanent residue in the growth medium. Dispersing and emulsifying agents which can be employed in liquid compositions include condensation products of alkylene oxides with phenols and organic acids, alkyl aryl sulfonates, polyoxyalkylene derivatives or sorbitol esters, sugar esters, complex ether alcohols, mahogany soaps and the like. The surface active agents are generally employed in the amount of from about 1 to about 20 percent by weight of the oxidized diaminophosphinyl sulfur derivatives and preferably in an amount of from about 1 to about 10 weight percent on the same basis.

Solid compositions containing the active one or more oxidized diaminophosphinyl sulfur derivatives can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with a solid one or more oxidized diaminophosphinyl sulfur derivatives; or wet with a liquid one or more oxidized diaminophosphinyl sulfur derivatives; or wet with a solution or dispersion of a solid or liquid one or more oxidized diaminophosphinyl sulfur derivatives in a volatile organic solvent. Depending upon the proportions of ingredients, these compositions can be employed without further modification or be considered concentrates and subsequently further diluted with solid surface active dispersing agents, talc, chalk, gypsum, bentonite, diatomaceous earth, fullers earth, or the like to obtain the desired treating composition. Furthermore, such concentrate compositions can be dispersed in water with or without added dispersing agent or agents to prepare aqueous soil treating compositions.

The required amount of the one or more oxidized diaminophosphinyl sulfur derivatives contemplated herein may be applied per acre treated in from about 1 to about 200 gallons or more of liquid carrier and/or diluent or in from about 5 to about 500 pounds of inert solid carrier and/or diluent. The concentration in the liquid concentrate will usually vary from about 10 to about 95 percent by weight and in the solid formulations from about 0.5 to about 90 percent by weight. Satisfactory sprays, dusts, or granules for general use contain from about ¼ to about 15 pounds of active one or more oxidized diaminophosphinyl sulfur derivatives per acre.

The compounds contemplated herein prevent or retard the urease catalyzed hydrolysis of urea, and they have relatively high residual activity. With respect to plants they have a high margin of safety in that when used in sufficient amount to inhibit the activity of urease, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable urease inhibiting characteristic of the compounds or impart undesirable characteristics, for instance, phytotoxicity, to the compounds. The compounds are so chemically inert that they are compatible with substantially any other constituents of the spray schedule, and they may be used in the soil, upon the seeds, or the roots of plants without injuring either the seeds or roots of plants.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, pharmaceutical applications, diaper treatment, urease inhibition in mammalian urinary tracts, and the like. It should be noted that while all of the above-identified compounds exhibit urease inhibiting activity, the particular active compound employed in one application may not necessarily be useful in another application. Thus, in the selection of a particular active compound for use in an application, such factors are toxicity of the compound, the environment in which the compound will be used, level of urease inhibition desired and the like must be considered in selecting a particular compound for use.

Diaminophosphinyl compounds which are useful as urease inhibitors in the composition of this invention are those of the formula:

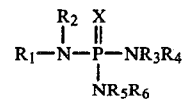

wherein:
X is oxygen or sulfur;
R₁ is

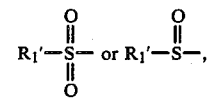

wherein
R₁' is amino or substituted or unsubstituted alkyl, aryl wherein permissible substituents are selected from the group consisting of one or more alkyl, aryl, halogen, trihalomethyl, nitro, cyano, alkanoyl, alkylcarboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl groups;
R₂ is hydrogen, or substituted or unsubstituted alkyl or aryl where permissible substituents are as in R₁ above; and
R₃, R₄, R₅ and R₆ are the same or different and are hydrogen or alkyl having from about 1 to about 4 carbon atoms.

Examples of R₁' include methyl, ethyl, isopropyl, tert-butyl, n-octyl, cyclohexyl, trichloromethyl, trifluoromethyl, 2-chloroethyl, phenyl, p-tolyl, 4-nitrophenyl, 3-chlorophenyl, 2-nitrophenyl, N,N-diphenylamino, 4-morpholine, pentamethyleneamino, N,N-dicyclohexylamino, N-diaminophosphinyl, 4-[O-(diaminophosphinyl)phenyl], 4-[N-(diaminophosphinyl)phenyl], 3-cyanophenyl, and the like.

Examples of R₂ include hydrogen, methyl, ethyl, phenyl, 2-chloroethyl, 4-nitrophenyl, 3-methyoxyphenyl, 2-methylmercaptoethyl, and the like.

Examples of R₃, R₄, R₅, and R₆ include hydrogen, methyl, ethyl, n-propyl, isopropyl, and tert-butyl.

Specific examples of other such compounds which would be expected to be good urease inhibitors include:
N-(Diaminophosphinyl)-4-methoxybenzenesulfonamide
N-(Diaminophosphinyl)-4-nitrobenzenesulfonamide
N-(Diaminophosphinyl)-3-chlorobenzenesulfonamide
N-(Diaminophosphinyl)methylsulfonamide
N-(Diaminophosphinyl)ethylsulfonamide
N-(Diaminophosphinyl)trichloromethylsulfonamide
N-(Diaminophosphinyl)trifluoromethylsulfonamide
N-(Diaminophosphinyl)sulfamide
N-(Diaminophosphinyl)-N'-methylsulfamide
N-(Diaminophosphinyl)-N',N'-diethylsulfamide
N-(Diaminophosphinyl)-N'-ethylsulfamide
N-(Diaminophosphinyl)-N',N'-dimethylsulfamide
N-(Diaminophosphinyl)-N',N'-dipropylsulfamide
N-(Diaminophosphinyl)-4-morpholinesulfamide
N-(Diaminophosphinyl)-N',N'-pentamethylenesulfamide
N-(Diaminophosphinyl)-N'-cyclohexylsulfamide
N-(Diaminophosphinyl)-N'-phenylsulfamide N-(Diaminophosphinyl)-N',N'-diphenylsulfamide
N-(Diaminophosphinyl)-N'-methylbenzenesulfonamide
N-(N'-Methyldiaminophosphinyl)benzenesulfonamide
N-(N',N''-Diethyldiaminophosphinyl)-4-toluenesulfonamide
N-(N',N''-Dimethyldiaminophosphinyl)benzenesulfonamide bis-N-(Diaminophosphinyl)sulfamide
N-(Diaminothiophosphinyl)benzenesulfonamide
N-(Diaminothiophosphinyl)-p-toluenesulfonamide
N-(Diaminothiophosphinyl)-N',N'-diethylsulfamide
N-(Diaminothiophosphinyl)-N'-butylsulfamide
N-(Diaminothiophosphinyl)-N'-methylbenzenesulfonamide
N-(N'-Methyldiaminothiophosphinyl)-N-methylbenzenesulfonamide
N-(Diaminothiophosphinyl)trichloromethylsulfonamide
N-(Diaminothiophosphinyl)trifluoromethylsulfonamide
N-(Diaminothiophosphinyl)methylsulfonamide
N-(Diaminothiophosphinyl)-N-tert-butylpropylsulfonamide
N-(N'-Methyldiaminothiophosphinyl)ethylsulfonamide bis-N-(Diaminothiophosphinyl)sulfamide
N-(Diaminophosphinyl)-N'-(2-chloroethyl)sulfamide
N-(Diaminophosphinyl)-N-(2'-methylmercaptoethyl)benzenesulfonamide
N-(Diaminophosphinyl)-N-(3'-methoxyphenyl)-4-toluenesulfonamide
N-(Diaminophosphinyl)benzenesulfinamide
N-(Diaminophosphinyl)-4-toluenesulfinamide
N-(Diaminophosphinyl)-3-methoxybenzenesulfinamide
N-(Diaminophosphinyl)-2-nitrobenzenesulfinamide
N-(Diaminophosphinyl)-4-chlorobenzenesulfinamide
N-(Diaminophosphinyl)-N-methyl-4-cyanobenzenesulfinamide
N-(Diaminophosphinyl)-N-ethyl-3-trichloromethylbenzenesulfanomide
N-(Diaminophosphinyl)-4-trifluoromethylbenzenesulfonamide
N-(Diaminophosphinyl)-N-phenylbenzenesulfinamide
N-(Diaminophosphinyl)-N'-methyl-4-methylmercaptobenzesulfanimide
N-(Diaminophosphinyl)-4-(N',N'-dimethylaminobenzenesulfinamide
N,4-bis-Diaminophosphinyl)sulfanilamide
N,O-bis-(Diaminophosphinyl)-4-hydroxybenzenesulfonamide
N,S-bis-(Diaminophosphinyl)-3-mercaptobenzenesulfonamide
N-(Diaminophosphinyl)-2-bromobenzenesulfonamide
N-(Diaminophosphinyl)-4-iodobenzenesulfonamide
N-(Diaminophosphinyl)-N-isopropyl-4-cyanobenzenesulfonamide
N-(Diaminophosphinyl)-4-acetylbenzenesulfonamide
N-(Diaminophosphinyl)-4-tert-butylbenzenesulfonamide
N-(Diaminophosphinyl)-3-(N',N'-dimethylamino)benzenesulfonamide
N-(Diaminophosphinyl)-6-methoxycarbonyl-n-hexylsulfamide
N,N-bis-(Diaminophosphinyl)-4-carbamoylbenzenesulfonamide
N-(Diaminophosphinyl)-tert-butylsulfinamide
N-(Diaminophosphinyl)trichloromethylsulfinamide
N-(Diaminothiophosphinyl) benzenesulfinamide
N-(Diaminothiophosphinyl)-4-toluenesulfinamide
N-(Diaminothiophosphinyl)-3-nitrobenzenesulfinamide
N-(Diaminothiophosphinyl)-2-ethoxybenzenesulfinamide
N-(Diaminothiophosphinyl)-N-methyl-4-chlorobenzenesulfinamide
N-(Diaminothiophosphinyl)-N-ethyl-3-toluenesulfinamide
N-(Diaminothiophosphinyl)-4-trichloromethylbenzenesulfinamide
N-(N''-Methyldiaminothiophosphinyl)-N'-methylbenzenesulfinamide
N-(N'-Methyldiaminothiophosphinyl)-N-propylbenzenesulfinamide
N-(Diaminothiophosphinyl)-N,N',N'-trimethylsulfamide
N-(Diaminothiophosphinyl)-N'-benzyl-N'-methylsulfamide
N-(Diaminothiophosphinyl)-N'-ethyl-N-methylsulfamide
N-(Diaminothiophosphinyl)-N'-phenyl-N-isopropylsulfamide
N-(Diaminothiophosphinyl)-N'-tert-butyl-N-ethylsulfamide
N-(Diaminothiophosphinyl)-N',N'-dibutyl-N-ethylsulfamide
N-(Diaminothiophosphinyl)-N'-phenyl-N-propylsulfamide
N-(Diaminothiophosphinyl)-N-butyl-N',N'-dimethylsulfamide
N-(Diaminothiophosphinyl)-tert-butylsulfinamide
N-(Diaminothiophosphinyl)trifluoromethylsulfinamide
N-(Diaminothiophosphinyl)-N'-methyl-N'-octylsulfamide
N-(N''-Methyldiaminothiophosphinyl)-N',N'-diisopropylsulfamide Preferred for use in the practice of this invention are compounds of the aforementioned generic formula in which X is oxygen.

Particularly preferred for use in the practice of this invention are compounds of the aforementioned generic formula in which:
X is oxygen;
$R_1$ is $$R_1'-\underset{\underset{O}{\|}}{\overset{\overset{O}{\|}}{S}}-,$$

wherein:
$R_1'$ is alkyl, cycloalkyl, phenyl, alkylphenyl, or phenylalkyl;
$R_2$ is hydrogen, or $R_1'$; and
$R_3$, $R_4$, $R_5$ and $R_6$ are hydrogen.

Amongst these particularly preferred compounds most preferred are those compounds is which:
X is oxygen;
$R_1$ is $$R_1'-\underset{\underset{O}{\|}}{\overset{\overset{O}{\|}}{S}}-;$$

wherein
$R_1'$ is alkyl having from about 1 to 7 carbon atoms, phenyl, or phenylalkyl or alkylphenyl having from about 7 to about 12 carbon atoms;

$R_2$ is hydrogen or $R_1$; and $R_3$, $R_4$, $R_5$ and $R_6$ are hydrogen.

Especially effacious compounds for use in practice of this invention are N-(diaminophosphinyl)-p-toluenesulfonamide and N-(diaminophosphinyl)benzenesulfonamide.

Compounds for use in the practice of this invention in which X is oxygen can be conveniently prepared in accordance with the following Reaction Scheme A:

Reaction Scheme A

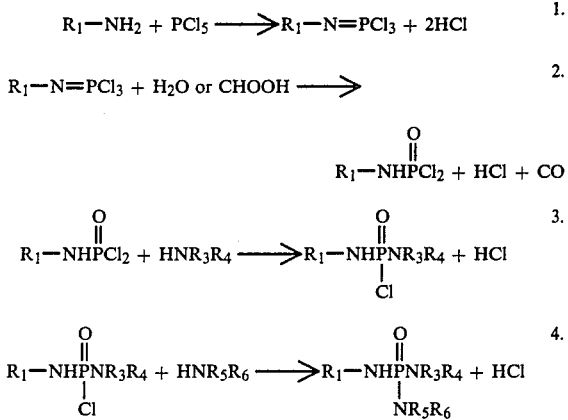

wherein $R_1$, $R_3$, $R_4$, $R_5$ and $R_6$ are as identified hereinabove.

Alternatively, compounds for use in the practice of this invention can be prepared according to the following Reaction Scheme B:

Reaction Scheme B

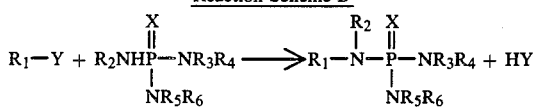

wherein $R_1$, $R_2$, $R_3$, $R_4$, $R_5$ and $R_6$ are as described above, and Y is a leaving group, such as flouride, chloride, bromide, iodide, alkylester, or the like.

Examples of compounds prepared by Reaction Scheme A are given in Nakanishi, M.; Oe, Ti; Japan Pat. No. 7379 (1967); Chem. Abstr. 1967, 67, 81947X. Examples of the preparation of sulfonylphosphoramidic dichlorides, sulfamoylphosphoramidic dichlorides and sulfonylbis(phosphoramidic trichlorides) are summarized by Nielsen, M. L. in "Developments in Inorganic Nitrogen Chemistry", Cobern, C. B., ed., Elsevier Publishing Co., New York, 1966, Ch V, pp 394, 436-37, and 448-49. The preparation of N,N-dialkylsulfamides is disclosed by Vandi, A. and Moeller, T. in "Inorganic Synthesis," Holtzshaw, H. F., Jr., ed., McGraw-Hill Book Co., New York, 1966. Vol VIII, pp 111–116, and references cited therein. The preparation of dialkylamides of (trichlorophosphoranylidene)sulfamic acids is described by Vandi, A. and Moeller, T., ibid., pp 116–119, and cited references therein. The preparation of bis(trichorophosphoranylidene)sulfamide is described by Vandi, A. and Moeller, T., ibid., pp 119–121, and references cited therein.

Briefly stated, in each step of the above reaction schemes, substantially equal molar amounts or excesses of the reactants are contacted neat or in an inert solvent. Useful inert reaction solvents include ethyl ether, carbon tetrachloride, methylene chloride, glyme, benzene, dioxane, toluene, xylene, tetrahydrofuran, methyl sulfoxide, dimethylformamide and the like.

In those reaction steps in which hydrogen chloride is produced an acid acceptor can be used.

The hydrogen chloride acid acceptor employed is a basic material which can be either an inorganic or organic base. Suitable inorganic bases include alkali metal carbonates such as sodium carbonate, potassium carbonate and the like. Organic bases which are useful and preferred for use in this invention are tertiary amines, as for example pyridine, lutidine, 1,4-diazabicyclo[2.2.2]octane, isoquinoline, quinoline, N-methylpiperidine, trimethylamine, triethylamine, and the like.

Reaction temperatures and pressures are not critical. The reaction can be conveniently carried out at a temperature of from about $-80°$ C. to about $200°$ C., but is preferably carried out at a temperature of from about $-30°$ C. to about $150°$ C. The reaction can be carried out at atmospheric, sub-atmospheric or super-atmospheric pressure. For convenience, however, the reaction is carried out at atmospheric or autogeneous pressure.

The order in which the reactants are reacted indicated in the reaction scheme is for illustrative purposes only, and the order of the reactions is not critical. The exact proportions of the reactants are not critical, some of the desired product can be obtained when the reactants are employed in any proportions.

Reaction times are not critical and can be varied widely depending on such factors as the reaction temperature, reactivity of the reactants, and the like. The reaction mixture is usually held within the desired reaction temperature range for a period of time, conveniently from about 30 minutes to about 72 hours before cooling. Good yields are obtained with reaction times of from 1 to about 8 hours.

After the reactions have gone substantially to completion, the product can be separated by such conventional procedures as evaporation, and purified by conventional procedures such as distillation and extraction. The product separated as described above can be employed in the control of urease in the soil or in other applications in accordance with this invention or may be further purified by conventional procedures such as extraction and distillation.

The following specific examples are presented to more particularly illustrate the invention.

EXAMPLE I

Preparation of N-(Diaminophosphinyl)-p-toluene-sulfonamide

A mixture of 51.4 g (0.300 mol) of p-toluenesulfonamide, 62.5 g (0.300 mol) of phosphorus pentachloride, and 500 mL of carbon tetrachloride was prepared under a nitrogen atmosphere in a dry 1000 mL, round bottom flask fitted with a mechanical stirrer and a condenser attached to a sodium hydroxide trap. The stirred mixture was gradually heated to 75° C. During this process hydrogen chloride steadily began to evolve. The mixture was heated for 60 h at 75° C. during which time gas evolution ceased and the solution became homogeneous. Upon cooling, however, the reaction mixture gelled into a slightly pink solid. The flask was re-warmed to 55° C. to redissolve the solid, the heating bath was removed, and 11.8 mL (14.4 g, 0.315 mol) of formic acid was added dropwise over a 20 min period.

Gases were vigorously evolved during this process and the color of the solution became yellow. The solution was stirred for another 2 h without external heating and then for 1 h at 55° C. The mixture was cooled to ambient temperature causing two layers to form in the flask. Analysis of each layer, however, showed them to be substantially the desired product, and, upon standing under nitrogen, each layer crystallized into a solid, mp 114°–118° C. and 118°–121° C. (upper and lower layers, respectively). The solids, 64 g from the upper layer and 28 g from the lower layer, were combined and extracted with 1200 mL of hot carbon tetrachloride. The mixture was filtered free from 5–10 g of residue, and 46.7 g (54%) pure p-toluenesulfonylphosphoramidic dichloride, mp 115.5°–117.5° C. (lit. mp 115°–118° C.) was obtained by allowing the filtrate to crystallize.

$^1$H NMR (CDCl$_3$): δ 8.82 (S, 1H, N$\underline{H}$), 7.83 (d, J=8 Hz, 2H, Ar$\underline{H}$), 7.28 (d, J=8 Hz, 2H, Ar$\underline{H}$), and 2.43 ppm (s, 3H, $\underline{C}$H$_3$).

The p-toluenesulfonylphosphoramidic dichloride (46.7 g, 0.162 mol) was dissolved in 200 mL of ether and added dropwise over a 2 h period to a well stirred solution of 75 mL of ammonia (about 3 mol) in 300 mL of ether at −30° to −35° C. The mixture was stirred for another 1.5 h while allowing the ammonia to maintain itself at reflux, and then for another 30 min under a nitrogen purge to remove excess ammonia. The still cool mixture was filtered, and the resulting white solid was washed well with ether. After being dried under nitrogen, 59.4 g (80%) of white solid composed of 70% (by weight) of N-(diaminophosphinyl)-p-toluenesulfonamide and 30% (by weight) of ammonium chloride was obtained. Since the desired product was insoluble in chloroform and related solvents, this mixture was used directly in urease inhibition studies.

$^1$H NMR (D$_2$O): δ 7.80 (d, J=8 Hz, 2H, Ar$\underline{H}$), 7.35 (d, J=8 Hz, 2H, Ar$\underline{H}$), and 2.38 ppm (s, 3H, $\underline{C}$H$_3$).

$^{31}$P NMR (D$_2$O): δ 10.4 ppm.

$^{13}$C NMR (Proton Decoupled in D$_2$O): δ 21.31 (s, 1C, $\underline{C}$H$_3$), 126.41 (s, 2C, Ar$\underline{C}$ ortho to SO$_2$NH—), 130.22 (s, 2C, Ar$\underline{C}$ meta to S$\overline{O}_2$NH—), 142.29 (s, 1C, Ar$\underline{C}$ ipso to SO$_2$$\overline{N}$H—), and 143.42 ppm (s, 1C, Ar$\underline{C}$ para to SO$_2$NH—).

Mass Spectrum (70 eV) of sample derivatized with "Methyl-8" reagent (DMF-Dimethylacetal) corresponding to p-CH$_3$C$_6$H$_4$SO$_2$NH-P(O)[N=CHN(CH$_3$)$_2$]$_2$: m/e 359 (M+), 295 (M+—SO$_2$), 189, 162, and 135. A peak at m/e 373 with a fragment at 309 was also present, and indicated that a methoxylated derivative was also formed.

Infrared (KBr): 3700-2500 (br, s, NH & NH$_4$Cl, 1630 (w), 1565 (s), 1400 (s), 1210 (s), 1078 (s), 940 (s), 755 (w), 729 (w), 690 (w), 610 (w), 510 (m), and 360 cm$^{-1}$ (m).

EXAMPLE II

Preparation of N-(Diaminophosphinyl)benzenesulfonamide

Into a 65 mL round bottom flask containing a stirrer was suspended 4.80 g (50 mmol) of phosphoric triamide in 20 mL of chloroform. To this was added 4.04 mL of pyridine (50 mmol). An addition funnel was placed on top of a condenser which was then attached to the flask. The system was purged with nitrogen, and 6.38 mL (50 mmol) of benzenesulfonyl chloride in 10 mL of chloroform was placed in the addition funnel. The benzenesulfonyl chloride solution was added dropwise over a 15 min period to give a somewhat exothermic reaction and a light yellow color. After stirring for 1 h at room temperature, the flask was then heated at 55°–60° C. for 60 h. The mixture was then cooled, and the resulting solids were broken-up, collected by filtration, washed well with 3×50 mL of chloroform, and dried under nitrogen to give 6.38 g (55%) of white product. The $^1$H NMR in D$_2$O showed two aromatic multiplets centered at w 7.87 and 7.68 ppm as well as about 20% pyridine hydrochloride as an impurity.

EXAMPLE III

Efficacy tests were conducted to evaluate the efficacy of certain representative oxidized sulfur derivatives of diaminophosphinyl compounds as urease inhibitors. The inhibition tests were run in New York (Cazenovia Silt loam, pH 7.3) and Wisconsin (Plano silt loam pH 5.3) soils. Evaluations (run in triplicate) consisted of applying 800 micrograms of the test compound in 5 mL of water and 42.8 mg of urea in 1 mL of water to 20 g of air-dry soil in a glass bottle. The bottle was capped with perforated aluminum foil and incubated at 25° C. for three days prior to extraction with 100 mL of a 2M potassium chloride solution containing 0.5 mg of phenylmercuric acetate. The extracts were then analyzed for remaining urea using an autoanalyzer. Percent inhibition was calculated as $$\% \text{ Inhibition} = \left(1 - \frac{A - B}{A - C}\right) \times 100\%$$

where A is urea recovered from unincubated sample (urea added to soil and immediately extracted); B is urea recovered from inhibited sample; and C is urea recovered from the control (uninhibited sample).

The results of these test are set forth in the following Table I.

TABLE I

| Experiment Number | Compound | % Inhibition 40 Micrograms per gram soil | |
|---|---|---|---|
| | | Cazenovia pH 7.3 | Wisconsin pH 5.3 |
| 1. | N—(Diaminophosphinyl)-p-toluenesulfonamide | 86 | 51 |
| 2. | N—(Diaminophosphinyl)-benzenesulfonamide | 91 | 23 |

What is claimed is:

1. A urease inhibiting composition comprising a carrier and a urease inhibiting effective amount of one or more compounds of the formula:

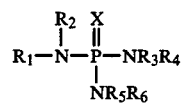

wherein:

X is oxygen or sulfur;

R$_1$ is

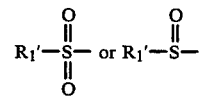

wherein;

$R_1'$ is amino or substituted or unsubstituted alkyl, aryl wherein permissible substituents are selected from the group consisting of one or more alkyl, aryl, halogen, trihalomethyl, nitro, cyano, alkanoyl, alkylcarboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl groups; and $R_2$ is hydrogen, or substituted or unsubstituted alkyl or aryl wherein permissible substituents are selected from the group consisting of one or more alkyl, aryl, halogen, trihalomethyl, nitro, cyano, alkanoyl, alkylcarboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl groups; and $R_3$, $R_4$, $R_5$ and $R_6$ are the same or different and are hydrogen or alkyl having from about 1 to about 4 carbon 2. A composition according claim 1 wherein X is oxygen.

3. A composition according to claim 1 wherein X is sulfur.

4. A composition according to claim 1 wherein: $R_1$ is

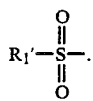

5. A composition according to claim 4 wherein $R_1'$ is alkyl, cycloalkyl, phenyl, phenylalkyl or alkylphenyl.

6. A composition according to claim 5 wherein $R_1'$ is phenyl or alkylphenyl having from about 7 to about 12 carbon atoms.

7. A composition according to claim 6 wherein $R_1'$ is alkylphenyl.

8. A composition according to claim 1 wherein $R_2$ is hydrogen or a substituent selected from the group consisting of permissible $R_1'$ substituents.

9. A composition according to claim 8 wherein $R_2$ is hydrogen.

10. A composition according to claim 1 wherein $R_3$, $R_4$, $R_5$ and $R_6$ are hydrogen.

11. A composition according to claim 1 wherein said one or more compounds are selected from the group consisting of N-(diaminophosphinyl)-p-toluenesulfonamide and N-(diaminophosphinyl)benzenesulfonamide.

12. A composition according to claim 1 wherein said urease inhibiting amounts is at least about 0.00001 weight percent based on the total weight of the composition.

13. A composition according to claim 12 wherein said amount is from about 0.0001 to about 98 weight percent.

14. A composition according to claim 13 wherein said amount is from about 0.002 to about 50 weight percent.

15. A composition according to claim 14 wherein said amount is from about 0.01 to about 20 weight percent.

16. An fertilizer composition which comprises a carrier, urea and/or one or more urea precursor compounds capable of forming urea in situ when subjected to the use conditions of the composition, and a urease inhibiting effective amount of one or more compounds of the formula:

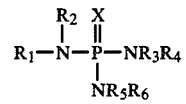

wherein:
X is oxygen or sulfur;
$R_1$ is

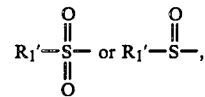

wherein
$R_1'$ is amino or substituted or unsubstituted alkyl or aryl wherein permissible substituents are selected from the group consisting of one or more alkyl, aryl, halogen, trihalomethyl, nitro, cyano, alkanoyl, alkylcarboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl;

$R_2$ is hydrogen, or substituted or unsubstituted alkyl or aryl wherein permissible substituents are selected from the group consisting of one or more alkyl, aryl, halogen, trihalomethyl, nitro, cyano, alkanoyl, alkylcarboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl; above; and $R_3$, $R_4$, $R_5$ and $R_6$ are the same or different and are hydrogen or alkyl having from about 1 to about 4 carbon atoms.

17. A composition according to claim 16 wherein X is oxygen.

18. A composition according to claim 16 wherein X is sulfur.

19. A composition according to claim 16 wherein $R_1$ is

20. A composition according to claim 19 wherein $R_1'$ is alkyl, cycloalkyl, phenyl, phenylalkyl or alkylphenyl.

21. A composition according to claim 19 wherein $R_1'$ is phenyl or alkylphenyl having from about 7 to about 12 carbon atoms.

22. A composition according to claim 21 wherein $R_1'$ is alkylphenyl.

23. A composition according to claim 16 wherein $R_2$ is hydrogen or a substituent selected from the group consisting of permissible $R_1$ substituents.

24. A composition according to claim 23 wherein $R_2$ is hydrogen.

25. A composition according to claim 16 wherein $R_3$, $R_4$, $R_5$ and $R_6$ are hydrogen.

26. A composition according to claim 16 wherein said one or more compounds are selected from the group consisting of N-(diaminophosphinyl)-p-toluenesulfonamide and N-(diaminophosphinyl)benzenesulfonamide.

* * * * *